United States Patent
Gagel et al.

(10) Patent No.: US 11,000,638 B2
(45) Date of Patent: May 11, 2021

(54) METHOD OF MONITORING THE BICARBONATE CONTENT AND THE SODIUM CONTENT OF A DIALYSIS SOLUTION

(71) Applicant: FRESENIUS MEDICAL CARE DEUTSCHLAND GMBH, Bad Homburg (DE)

(72) Inventors: Alfred Gagel, Litzendorf (DE); Tilman Stablein, Wurzburg (DE); Jochen Popp, Oberwerrn (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 169 days.

(21) Appl. No.: 16/321,834

(22) PCT Filed: Aug. 3, 2017

(86) PCT No.: PCT/EP2017/000942
§ 371 (c)(1),
(2) Date: Jan. 30, 2019

(87) PCT Pub. No.: WO2018/024373
PCT Pub. Date: Feb. 8, 2018

(65) Prior Publication Data
US 2019/0167879 A1    Jun. 6, 2019

(30) Foreign Application Priority Data

Aug. 3, 2016   (DE) .................... 10 2016 009 442.7

(51) Int. Cl.
*A61M 1/16*     (2006.01)
*A61K 33/00*    (2006.01)
*G01N 27/07*    (2006.01)

(52) U.S. Cl.
CPC .......... *A61M 1/1607* (2014.02); *A61K 33/00* (2013.01); *A61M 1/165* (2014.02);
(Continued)

(58) Field of Classification Search
None
See application file for complete search history.

(56) References Cited

U.S. PATENT DOCUMENTS 3,633,820 A * 1/1972 Weissohn .................. F27B 1/26
                                                    236/46 R
4,399,036 A * 8/1983 Babb .................... A61M 1/1656
                                                    210/638
(Continued)

FOREIGN PATENT DOCUMENTS

EP          0311848 A2    4/1989
EP          0597817 A2    5/1994
WO       2014173747 A1   10/2014

OTHER PUBLICATIONS

Purdue Online Writing Lab—Which vs That, https://owl.purdue.edu/owl/general_writing/grammar/that_vs_which.html (downloaded Sep. 17, 2020). (Year: 2020).*

(Continued)

*Primary Examiner* — Chester T Barry
(74) *Attorney, Agent, or Firm* — Kilyk & Bowersox, P.L.L.C.

(57) ABSTRACT

The present invention relates to a method of monitoring the bicarbonate content and the sodium content of a dialysis solution, wherein the dialysis solution is prepared while adding a bicarbonate component and an acidic sodium component, and wherein the method comprises the following steps:

a. adding the acidic sodium component and measuring the conductivity ($LF_{ist,Na}$);

(Continued)

b. adding the bicarbonate component and measuring the increase in conductivity ($\Delta LF_{ist,BiC}$) caused by adding the bicarbonate component;

c. determining the increase in conductivity ($\Delta LF_{exp,Bic}$) expected due to the addition of the bicarbonate component;

d. checking whether the measured increase in conductivity ($\Delta LF_{ist,Bic}$) lies in an expected range of the increase in conductivity ($\Delta LF_{exp,Bic}$);

e. determining the total conductivity ($LF_{exp,D}$) expected after the addition of the bicarbonate component and of the acidic sodium component;

f. measuring the total conductivity ($LF_{ist,D}$) after the addition of the bicarbonate component and of the acidic sodium component; and g. checking whether the measured total conductivity ($LF_{ist,D}$) lies in an expected range of the total conductivity ($LF_{exp,D}$), wherein the measurement of the conductivity in accordance with step a.; the measurement of the increase in conductivity in accordance with step b.; and the measurement of the total conductivity in accordance with step f. are carried out by one and the same conductivity measurement cell.

15 Claims, 2 Drawing Sheets

(52) U.S. Cl.
CPC ........ *A61M 1/1613* (2014.02); *A61M 1/1656* (2013.01); *G01N 27/07* (2013.01); *A61M 2205/18* (2013.01); *A61M 2205/3317* (2013.01)

(56) References Cited

U.S. PATENT DOCUMENTS

| | | | | |
|---|---|---|---|---|
| 4,814,073 | A * | 3/1989 | Shouldice | A61M 1/1668 210/321.69 |
| 4,895,657 | A | 1/1990 | Polaschegg | |
| 5,932,110 | A * | 8/1999 | Shah | A61M 1/1609 210/739 |
| 6,395,880 | B1 * | 5/2002 | Linnau | C07K 14/8128 530/393 |
| 7,544,301 | B2 * | 6/2009 | Shah | A61K 33/14 210/647 |
| 9,314,560 | B2 * | 4/2016 | Wiktor | A61M 1/287 |
| 2002/0088752 | A1 * | 7/2002 | Balschat | A61M 1/1656 210/646 |
| 2003/0194810 | A1 * | 10/2003 | Dotsch | G01R 33/46 436/18 |
| 2004/0254702 | A1 * | 12/2004 | Mueller | B62J 27/00 701/38 |
| 2005/0026202 | A1 * | 2/2005 | Edman | G01N 33/54353 435/6.11 |
| 2007/0178516 | A1 * | 8/2007 | Sosnowski | B01J 19/0093 435/6.11 |
| 2010/0117666 | A1 * | 5/2010 | Wada | G01N 27/447 324/705 |
| 2014/0319030 | A1 * | 10/2014 | Shah | A61K 31/19 210/96.2 |
| 2017/0348471 | A1 * | 12/2017 | Goto | A61B 5/0408 |

OTHER PUBLICATIONS

Examination Report issued in corresponding German Patent Application No. 10 2016 009 442.7 dated Apr. 20, 2017 (10 pages).

Deutsche Norm, "Medical electrical equipment—Part 2-16: Particular requirements for the basic safety and essential performance of haemodialysis, haemodiafiltraation and haemofiltration equipment," DIN EN 60601-2-16 (IEC 60601-2-16:2012), Feb. 2016, German version EN 60601-2-16:2015, 79 pages.

International Search Report and Written Opinion issued in corresponding International Patent Application No. PCT/EP2017/000942 (with English translation of International Search Report) dated Nov. 14, 2017 (14 pages).

* cited by examiner

METHOD OF MONITORING THE BICARBONATE CONTENT AND THE SODIUM CONTENT OF A DIALYSIS SOLUTION

This application is a National Stage Application of PCT/EP2017/000942, filed Aug. 3, 2017, which claims priority to German Patent Application No. 10 2016 009 442.7, filed Aug. 3, 2016.

The present invention relates to a method of monitoring the bicarbonate content and the sodium content of a dialysis solution, wherein the dialysis solution is prepared while adding a bicarbonate component and an acidic sodium component.

Hemodialysis is an important treatment method for chronic renal failure. In hemodialysis, the patient's blood to be purified is led along on one side of a membrane of a dialyzer. The dialysis solution, into which substances diffuse from the blood over the membrane due to a concentration gradient between the blood and the dialysis solution, is located on the other side of the membrane. To prevent vital substances being withdrawn from the patient continuously during the treatment, it is necessary to provide the dialysis solution with these substances in physiological concentrations. In this respect, primarily sodium and bicarbonate (hydrogen carbonate) are crucial in addition to the electrolytes calcium, magnesium and potassium.

It is known from the prior art to prepare the required dialysis solution from two concentrates while adding water. In this respect, one concentrate mainly contains sodium while the other concentrate primarily contains bicarbonate.

The dialysis standard IEC 60601-2-16 (3rd and 4th editions) requires an independent protection system which prevents any risk to patients arising from an incorrect composition of the dialysis solution.

A dialysis machine is known from EP 0 597 817 B1 which has a preparation device for the dialysis solution. The preparation device has a main line which is in communication with a water source and into which a first and second feed line open, wherein the first feed line is in communication with a sodium concentrate container and the second feed line is in communication with a bicarbonate concentrate container. The concentrates are admixed to the fluid flowing through the main line via pumps to obtain a dialysis solution ready to use. A conductivity measurement cell is arranged downstream of the opening of the concentrate containing sodium in the main line. A further conductivity measurement cell is located downstream of the opening of the bicarbonate concentrate in the main line. A third conductivity measurement cell is arranged between the balancing chamber and the dialyzer.

Such a dialysis machine suffers from the disadvantage of a comparatively complex design.

A dialysis machine is known from DE 34 16 057 A1 in which a conductivity measurement cell is arranged downstream of the openings of the concentrate lines into a main line. The conductivity measurement cell serves the determination of the conductivity of the dialysis solution flowing into the dialyzer. A check of the total conductivity can admittedly thus be carried out, but a monitoring of the bicarbonate content of the dialysis solution is not provided in DE 34 16 057 A1.

It is the underlying object of the present invention to further develop a method of the initially named kind such that a monitoring of the sodium content and of the bicarbonate content of the dialysis solution is possible in a manner which is as simple and as reliable as possible.

This object is achieved by a method having the features of claim 1.

The method accordingly comprises the following steps which can be carried out in the given (temporal) order, but also in any other possible order.

a. Adding the acidic sodium component and measuring the conductivity ($LF_{ist,Na}$);
b. adding the bicarbonate component and measuring the increase in conductivity ($\Delta LF_{ist,Bic}$) caused by adding the bicarbonate component;
c. determining the increase in conductivity ($\Delta LF_{exp,Bic}$) expected due to the addition of the bicarbonate component;
d. checking whether the measured increase of conductivity ($\Delta LF_{ist,Bic}$) lies in an expected range of the increase in conductivity ($\Delta LF_{exp,Bic}$);
e. determining the total conductivity ($LF_{exp,D}$) expected after the addition of the bicarbonate component and of the acidic sodium component;
f. measuring the total conductivity ($LF_{ist,D}$) after the addition of the bicarbonate component and of the acidic sodium component; and
g. checking whether the measured total conductivity ($LF_{ist,D}$) lies in an expected range of the total conductivity ($LF_{exp,D}$), wherein the measurement of the conductivity in accordance with step a.; the measurement of the increase in conductivity in accordance with step b.; and the measurement of the total conductivity in accordance with step f. are carried out by one and the same conductivity measurement cell.

In accordance with the invention, an expected increase of conductivity due to the addition of the bicarbonate component is compared with a measured increase of conductivity and a conclusion is drawn in this manner on whether the bicarbonate concentration of the dialysis solution is within the desired range.

The monitoring of the sodium concentration takes place on the basis of a comparison between the measured total conductivity, i.e. the measured conductivity of the dialysis solution after the addition of the acidic sodium component and of the bicarbonate component. A conclusion can be drawn on the basis of this comparison on whether the sodium concentration is within the desired range.

A single conductivity sensor is used for these conductivity measurements, which represents a simplification with respect to known arrangements. It is possible by means of the present method to monitor both the bicarbonate concentration and the sodium concentration with a single conductivity sensor.

The parameter is the total conductivity of the dialysis solution or its change over time. The method in accordance with the invention can be used to monitor the limits required by the standard for bicarbonate and sodium deviations of a dialysis solution, for example by two independent and/or different limit value windows. The dialysis solution is preferably obtained by the separate metering in of the components (acidic sodium component and bicarbonate component).

The term "acidic sodium component" comprises any desired arrangement of a medium containing sodium ions, in particular a concentrate which contains sodium ions and at least one acid. The sodium component preferably contains further electrolytes such as Ca, Mg, Cl, K and optionally further substances. Provision is preferably made that the sodium component primarily contains sodium ions.

The acidic sodium component is preferably the main source of sodium in the completed dialysis solution, i.e. the predominant portion of the sodium of the completed dialysis solution preferably originates from the acidic sodium component.

The term "bicarbonate component" covers any desired arrangement of a medium containing bicarbonate ions, in particular a concentrate containing bicarbonate ions. The bicarbonate component preferably contains electrolytes such as Na ions in addition to bicarbonate. Provision is preferably made that the bicarbonate component primarily contains bicarbonate ions.

The bicarbonate component is preferably basic.

In a preferred embodiment of the invention, the bicarbonate component does not contain any acid.

The term "measurement" used within the framework of the invention comprises the direct measurement of a parameter, e.g. of the conductivity, as well as also values on which measurements are based such as values which are obtained by subtraction of two directly measured values of the conductivity.

The term "adding/addition" used within the framework of the invention comprises the admixing of a component into another component such as into water and also the presentation of the component. The phrase "adding an acidic sodium component" is thus to be understood, for example, as both the case that the acidic sodium component of a different component such as RO water is added and the case that this component is presented, i.e. e.g. a mixture of a concentrate containing sodium and RO water.

In a conceivable embodiment of the invention, the acidic sodium component and water are mixed, are led part the conductivity measurement cell and their conductivity is measured. In a second step, the bicarbonate component can then be added and the total conductivity can be determined. The measurement of the increase in conductivity by the addition of the bicarbonate component can be carried out in that the measured conductivity which the mixture of water and the acidic sodium component has (before adding the bicarbonate component) is subtracted from the measured total conductivity.

If the measured increase in conductivity is outside a certain range, a conclusion can be drawn that the bicarbonate concentration does not correspond to the desired bicarbonate concentration.

If the measured total conductivity is outside a certain range, a conclusion can be drawn that the sodium concentration does not correspond to the desired sodium concentration. For the total conductivity of the dialysis solution is mainly sensitive toward changes of the sodium concentration.

In this manner, both the content of bicarbonate ions and the content of sodium ions can be monitored permanently or in interval during the preparation of the dialysis solution by means of a single conductivity sensor.

As stated above, a conceivable variant of the method comprises the acidic sodium component being added first and the measured increase in conductivity due to the addition of the bicarbonate component in accordance with step b. being obtained in that the measured conductivity after the addition of the acidic sodium component is deducted from the measured total conductivity.

The expected increase in conductivity in accordance with step c., i.e. the expected increase in conductivity due to the addition of the bicarbonate component, can be calculated from the substances of the bicarbonate component.

It is possible by the present invention to measure the bicarbonate concentration and also the sodium concentration, with limit value ranges of identical or different sizes being able to be defined for the check whether the concentrations are within desired ranges.

It is conceivable, for example, that the expected range for the bicarbonate concentration extends from a value 25% below the expected increase in conductivity up to a value 25% above the expected increase in conductivity. The desired value range for bicarbonate thus extends by 25% upward and downward in each case starting from the expected value.

For the sodium concentration, the expected range can extend, for example, from 5% below to 5% above an expected value for the total conductivity.

Other range limits are also generally conceivable and covered by the invention.

Provision is preferably made that the expected total conductivity is calculated from the substances of the acidic sodium component and of the bicarbonate component.

To be able to make changes to the concentrations while a patient is connected to the dialysis machine, provision can be made that the prepared dialysis solution is decoupled from the dialyzer of the dialysis machine from time to time for the monitoring of the bicarbonate content and of the sodium content of a dialysis solution on a change in concentration. A "calibration" of the dialysis solution can thus take place without the patient being influenced.

If the respective range is exceeded or fallen below, an alarm can be output and/or an output of corresponding information to a user can take place that the desired concentration is outside the desired value range.

It is conceivable in this respect that an alarm is triggered and/or the output of corresponding information takes place as soon as the range for the sodium content or the range for the bicarbonate content is exceeded or fallen below depending on which exceeding or falling below takes place the sooner. The monitoring window which is left first will thus output an alarm or other information.

The present invention furthermore relates to a dialysis machine and/or to a preparation device for a dialysis solution which has means which are suitable and designed to carry out the method in accordance with the invention.

The preparation device for preparing a dialysis solution from at least two components comprises a container having a bicarbonate component ("bicarbonate container") and a container having an acidic sodium component ("sodium container"), wherein the preparation device has a conductivity measurement cell, for example arranged downstream of the sodium container, for measuring the conductivity of the fluid after the addition of the acidic sodium component; a conductivity measurement cell, preferably arranged downstream of the bicarbonate container, for measuring the increase in conductivity caused by adding the bicarbonate component; and a conductivity measurement cell, preferably arranged downstream of the sodium container and of the bicarbonate container, for measuring the total conductivity of the dialysis solution containing the acidic sodium component and the bicarbonate component. The dialysis machine furthermore has a checking unit which is configured such that it checks whether the measured increase in conductivity caused by the addition of the bicarbonate component is in an expected range of the increase in conductivity and whether the measured total conductivity is in an expected range of the total conductivity, with the named conductivity measurement cells being one and the same conductivity measurement cell.

The preparation device preferably has an alarm unit and/or an output unit for outputting information to a user which is/are configured such that an alarm is triggered and/or information is output when the exceeding or falling below of the range is detected.

The preparation device can have a main line into which a feed line in communication with the bicarbonate container opens and into which a further feed line in communication with the sodium container opens. This main line can be in communication with a container or with a source for water, preferably for RO water.

The bicarbonate component and the acidic sodium component are thus metered into the fluid, in particular RO water, flowing through the main line. Pumps can be used for this purpose which convey the components from concentrate containers into the main line.

It is also conceivable and covered by the invention that the containers containing the components are flowed through. The preparation of the dialysis solution can thus take place, for example, such that RO water or another fluid provided for the preparation flows through the container containing the bicarbonate or containing the sodium and a solution containing bicarbonate or sodium is thus prepared. The other component can then be metered into this solution, which can take place, for example, by introducing a concentrate into a main line or by flowing through the concentrate container.

The conductivity measurement cell is preferably arranged downstream of both openings of the feed lines or such that both the total conductivity and the increase in conductivity caused by the addition of the bicarbonate can be measured.

The preparation device can have a bypass line which leads around relative to a dialyzer of a dialysis machine and through which the prepared dialysis solution is led at times. As stated above, it can be ensured in this manner that the completed dialysis solution is only used for the treatment when it has been calibrated correctly and the limit value windows have been set, i.e. when both the bicarbonate content and the sodium content are in the respective desired ranges.

The preparation device can have an in integral component of a dialysis machine or can also be configured as a unit separate from a dialysis machine.

The present invention furthermore relates to a dialysis machine having at least one preparation device in accordance with the invention.

Further details and advantages of the invention will be explained in more detail with reference to an embodiment shown in the drawing.

The embodiment described in the following represents a possibility of additionally monitoring with respect to the required limits by a conductivity measurement of the dialysis solution in a two-component system without more than one conductivity measurement cell having to be used for this purpose. It must be pointed out at this point that the invention is not restricted to adding exactly two components; more than two components can also be added.

In accordance with the invention, a bicarbonate component and an acidic sodium component can be metered in separately. The metering can take place, for example, into a line in which water, preferably RO water or a solution, flows which was obtained from a mixture of one of the components with water or RO water.

The expected total conductivity and the expected increase in conductivity after adding the bicarbonate component are to be calculated on the basis of the respective substances or on the basis of the conductivity of the dialysis solution to be theoretically expected.

Figure 1:
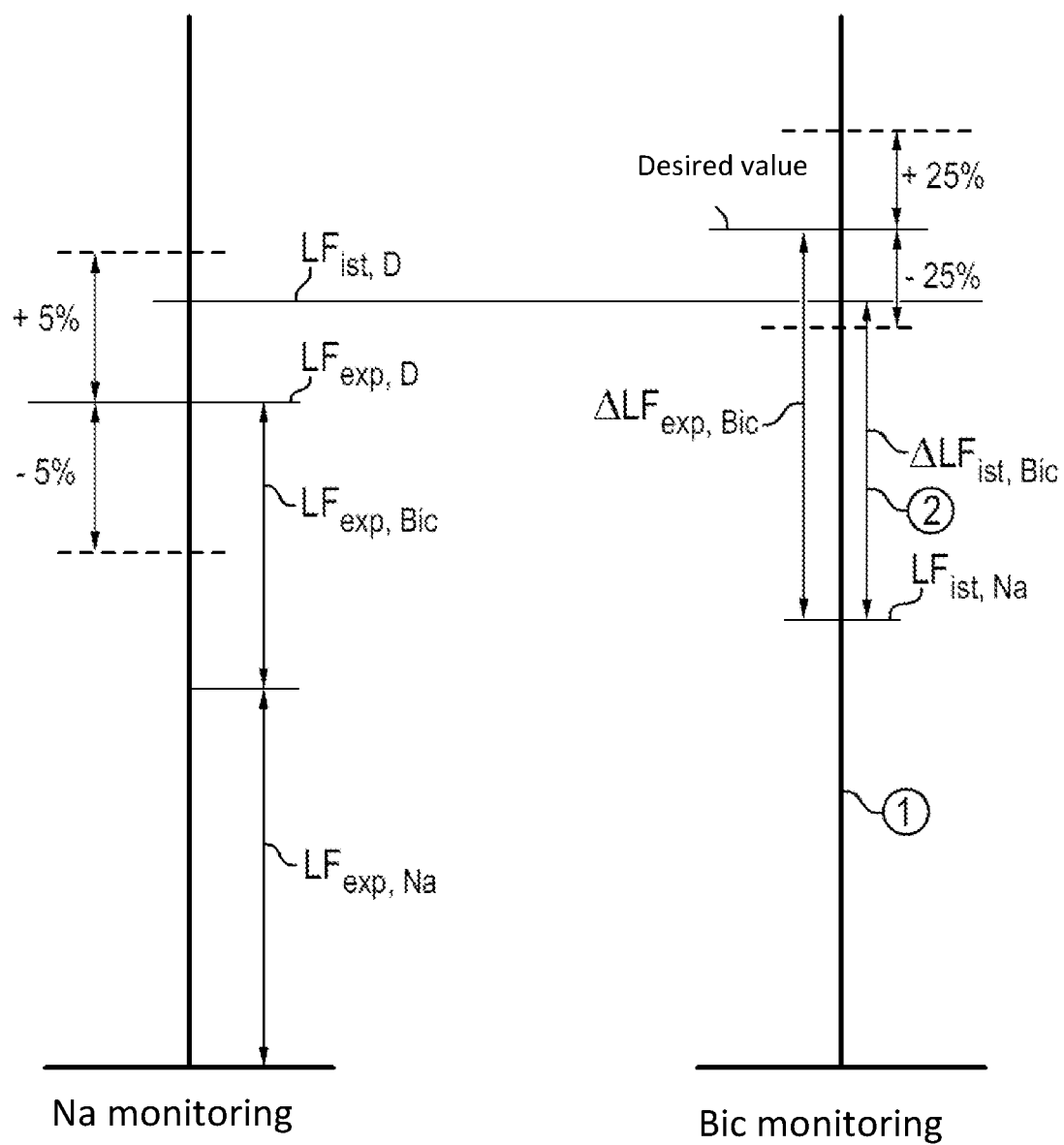
FIG. 1 shows a schematic representation of the sodium and bicarbonate monitoring by means of two independent limit value windows (ranges) using a single conductivity measurement cell.

In accordance with FIG. 1, the conductivity to be expected, i.e. the total conductivity $LF_{exp,D}$ of the completed dialysis solution to be expected is calculated from the latter's substances with the aid of a mathematical formula.

The operating system, i.e. the preparation device, in which the dialysis solution is mixed suffers from different tolerances. This tolerance chain can have the result that the actually measured total conductivity $LF_{ist,D}$ of the completed dialysis solution, i.e. the dialysis solution containing the acidic sodium component and the bicarbonate component, deviates from the theoretically calculated expected value $LF_{exp,D}$.

As can be seen from the left hand side of FIG. 1 ("Na monitoring"), the total conductivity $LF_{exp,D}$ to be expected is composed of the expected (nominal) conductivity of the acidic sodium component $LF_{exp,Na}$ and of the expected (nominal) conductivity of the bicarbonate component $LF_{exp,Bic}$.

A 5% deviation of the sodium concentration with respect to the calculated expected value $LF_{exp,D}$, i.e. from the desired value, can be determined by monitoring the total conductivity $LF_{exp,D}$ for a deviation of 5% shown at the left hand side of FIG. 1. The range in which the total conductivity may be thus amounts to 10% and extends in each case by 5% upward and downward from the expected value.

The right hand side of FIG. 1 ("Bic monitoring") has the following structure:

The conductivity $LF_{ist,Na}$ is the measured conductivity of the solution after the addition of the acidic sodium component.

The expected increase in conductivity by adding the bicarbonate component to this solution is marked by $\Delta LF_{exp,Bic}$ at the right hand side of FIG. 1. It is calculated from the difference between the expected total conductivity $LF_{exp,D}$ and the expected conductivity of the acidic sodium component $LF_{exp,Na}$.

The bicarbonate component typically contains sodium in addition to bicarbonate. The procedure is as follows in order not to have to take account of the influence of the acidic component containing sodium itself, of the metering of the acidic sodium component suffering from tolerances, and of additional interference parameters such as the basic conductivity of the water used in the calculation of the desired value of the conductivity of the bicarbonate component:

In a first step, only the acidic sodium component and the required water is metered in (Metering 1) and is led past the conductivity measurement cell. The conductivity $LF_{ist,Na}$ obtained in this respect contains all the tolerances of the operating system and serves as an offset for the monitoring limits of the bicarbonate which still have to be determined.

In the second step, the bicarbonate component is added (Metering 2) so that all the components are present and the dialysis solution is completely initially mixed. A measured total conductivity $LF_{ist,D}$ of the dialysis solution is adopted. The already determined conductivity of the dialysis solution containing sodium (without bicarbonate) $LF_{ist,Na}$ is deducted from the measured total conductivity $LF_{ist,D}$ and the actual contribution of the bicarbonate component $\Delta LF_{ist,Bic}$ to the total conductivity is thus measured.

$$\Delta LF_{ist,Bic} = LF_{ist,D} - LF_{ist,Na}$$

The offset of the acidic sodium component (including water and tolerances) determined in step 1 is thus eliminated from the measured total conductivity $LF_{ist,D}$ by calculation and the contribution of the bicarbonate component to the conductivity is determined in this manner.

The monitoring limits can be calculated from the increase in conductivity to be theoretically expected due to the addition of the bicarbonate component $\Delta LF_{exp,Bic}$ (desired value) and thus relate to the required desired value. In the embodiment in accordance with the right hand side of FIG. 1, the monitoring limits extend from a value 25% below $\Delta LF_{exp,Bic}$ to 25% above $\Delta LF_{exp,Bic}$, i.e. the permitted increase in conductivity caused by the addition of the bicarbonate solution lies in the interval $\Delta LF_{exp,Bic}*0.75$ to $\Delta LF_{exp,Bic}*1.25$.

When taking account of the limit values for the total conductivity, two independent monitoring windows thus result for sodium and bicarbonate which can detect the respective concentration deviations from the desired value in accordance with the demands of the standard.

To ensure a two-channel design, provision is preferably made that all the theoretical calculations of expected values are carried out by a protection system which is independent of the operating system of the dialysis machine.

Changes in the concentrations during the treatment such as the shift in the sodium concentration and/or bicarbonate concentration can be taken into account using the procedure in accordance with the invention. A repeat calibration of the system, i.e. the repeat preparation of a dialysis solution having correspondingly changed concentration values could take place, for example, during a bypass, i.e. during a hydraulic decoupling of the preparation device from the water part of the dialysis machine. A theoretical new calculation of the monitoring windows would also be conceivable without a repeat calibration on a change of the concentration under certain circumstances.

On a change of concentrate or on a canister change, the method in accordance with a first variant has to be carried out again. In the event that a somewhat larger uncertainty can be accepted, a theoretical new calculation of the bicarbonate limit window is possible on a change of the concentrate or on a canister change in accordance with a second variant. The sodium limit window can be calculated again at any time. The sodium concentration can furthermore always be measured again.

An abruptly occurring error in the metering in of the acidic sodium component can have the result due to the simultaneous monitoring of the sodium concentration and of the bicarbonate concentration by means of a single conductivity measurement cell that an alarm is triggered because the bicarbonate monitoring window has been left. Due to the fact that a single conductivity measurement cell, which measures the total conductivity of the dialysis solution in normal operation, cannot make any distinction as to the component from which the error emanates, the monitoring window which is left first will trigger an alarm. It can be precluded with the help of risk management that, for example, metering errors of the pumps conveying the components can occur in the opposite direction. This could result in a mutual cancellation of the errors in the conductivity under certain circumstances. Multiple errors are precluded from the viewpoint or risk management.

Figure 2:
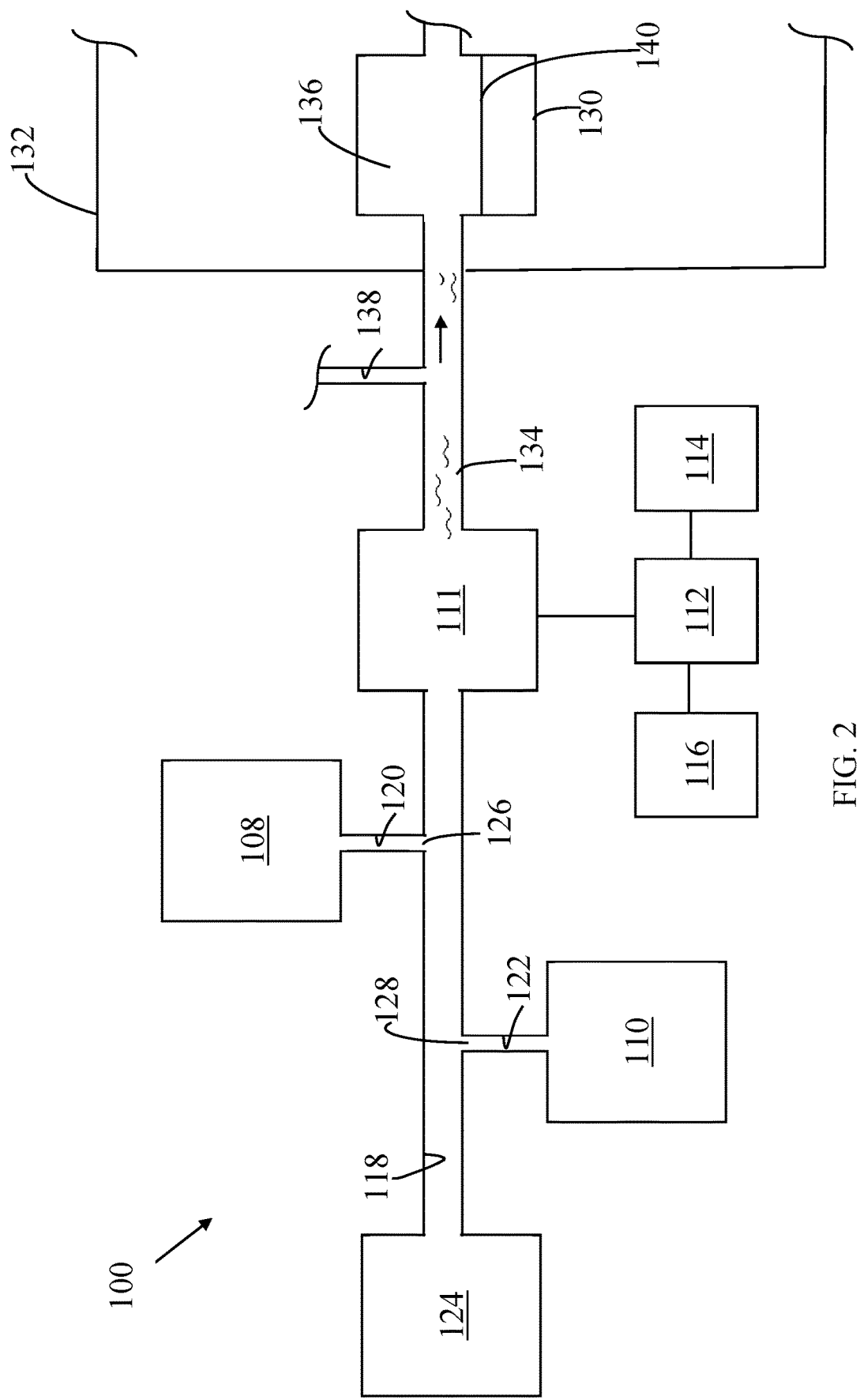
FIG. 2 shows a preparation device for preparing a dialysis solution from at least two components.

Referring to FIG. 2, a preparation device 100 prepares a dialysis solution 134 from at least two components. Preparation device 100 includes a container 108 having a bicarbonate component therein ("bicarbonate container,") and a container 110 having an acidic sodium component therein ("sodium container"). Preparation device 100 includes a conductivity measurement cell 111 having sensors 112 for measuring the increase in conductivity ($LF_{ist,Na}$) of dialysis solution 134 after the addition of the acidic sodium component, for measuring the increase in conductivity ($\Delta LF_{ist,Bic}$) of dialysis solution 134 after the addition of the component containing bicarbonate, and for the measuring the total conductivity ($LF_{ist,D}$) of dialysis solution 134 after the addition of both the acidic sodium component and the bicarbonate component. Conductivity measurement cell 111 is arranged downstream of sodium container 110 and downstream of bicarbonate container 108. Preparation device 100 is configured such that it checks whether the increase in conductivity ($\Delta LF_{ist,Bic}$) caused by the addition of the bicarbonate component is within an expected range of increase in conductivity ($\Delta LF_{exp,Bic}$) and whether the measured total conductivity ($LF_{ist,D}$) is within an expected range of total conductivity ($LF_{exp,D}$).

Preparation device 100 includes an alarm unit 114 and an output unit 116 for outputting information to a user and that are configured such that an alarm is triggered and information is output when conductivity exceeding or falling below a range is detected.

Preparation device 100 includes a main line 118 into which a feed line 120, that is in communication with bicarbonate container 108, opens at an opening 126. A feed line 122 in communication with sodium container 110 opens at an opening 128 into main line 118. Main line 118 is also in communication with a container 124 containing a source of water. Conductivity measurement cell 111 is arranged downstream of both openings 126 and 128 and feed lines 120 and 122.

A dialysis machine 132 is provided that comprises a dialyzer 130 having a dialysate side 136 separated from a blood side by a semi-permeable membrane 140. Preparation device 100 can be brought into fluid communication with dialyzer 130 of dialysis machine 132 so that prepared dialysis solution 134 flows through dialysate side 136 of dialyzer 130. Preparation device 100 also includes a bypass line 138 that leads around dialyzer 130 so that the prepared dialysis solution 134 can be led around dialyzer 136, at times.

It must be pointed out that the term "conductivity" includes every parameter which correlates with the conductivity or with the content of sodium and bicarbonate. The term "conductivity measurement cell" accordingly includes every sensor by means of which the conductivity or a parameter correlating therewith or with the content of sodium and bicarbonate can be measured.

The local order in which the acidic sodium component and the bicarbonate component are added in the hydraulic system of the dialysis machine during normal operation does not play any role for the method.

It is generally pointed out that all or some of the steps of the method in accordance with the invention can be carried out continuously and/or a multiple of times and/or cyclically and/or periodically.

The invention claimed is:
1. A method of monitoring the bicarbonate content and the sodium content of a dialysis solution, wherein the dialysis solution is prepared while adding a bicarbonate component and an acidic sodium component, and wherein the method comprises the following steps:
  a. adding the acidic sodium component and measuring the conductivity ($LF_{ist,Na}$);
  b. adding the bicarbonate component and measuring the increase in conductivity ($\Delta LF_{ist,Bic}$) caused by adding the bicarbonate component;
  c. determining the increase in conductivity ($\Delta LF_{exp,Bic}$) expected due to the addition of the bicarbonate component;
  d. checking whether the measured increase in conductivity ($\Delta LF_{ist,Bic}$) lies in an expected range of the increase in conductivity ($\Delta LF_{exp,Bic}$);
  e. determining the total conductivity ($LF_{exp,D}$) expected after the addition of the bicarbonate component and of the acidic sodium component;
  f. measuring the total conductivity ($LF_{ist,D}$) after the addition of the bicarbonate component and of the acidic sodium component; and
  g. checking whether the measured total conductivity ($LF_{ist,D}$) lies in an expected range of the total conductivity ($LF_{exp,D}$),
  wherein the measurement of the conductivity in accordance with step a.; the measurement of the increase in conductivity in accordance with step b.; and the measurement of the total conductivity in accordance with step f. are carried out by one and the same conductivity measurement cell.

2. The method in accordance with claim 1, characterized in that the acidic sodium component is added first; and in that the measurement of the increase in conductivity ($\Delta LF_{ist,Bic}$) in accordance with step b. is obtained in that the measured conductivity ($LF_{ist,Na}$) after the addition of the acidic sodium component is deducted from the measured total conductivity ($LF_{ist,D}$) in accordance with step f.

3. The method in accordance with claim 1, characterized in that the expected increase in conductivity ($\Delta LF_{exp,Bic}$) in accordance with step c. is calculated from the substances of the bicarbonate component.

4. The method in accordance with claim 1, characterized in that the expected range in accordance with step d. extends from a value 25% below the expected increase in conductivity ($\Delta LF_{exp,Bic}$) up to a value 25% above the expected increase in conductivity ($\Delta LF_{exp,Bic}$).

5. The method in accordance with claim 1, characterized in that the expected total conductivity ($\Delta LF_{exp,D}$) in accordance with step e. is calculated from the substances of the acidic sodium component and of the bicarbonate component.

6. The method in accordance with claim 1, characterized in that the expected range for the total conductivity extends from a value 5% below the expected total conductivity ($\Delta LF_{exp,D}$) up to a value 5% above the expected total conductivity ($\Delta LF_{exp,D}$).

7. The method in accordance with claim 1, characterized in that the prepared dialysis solution is decoupled from the dialyzer of a dialysis machine from time to time for monitoring the bicarbonate content and the sodium content of a dialysis solution on a change in concentration.

8. The method in accordance with one claim 1, characterized in that an alarm and/or an output of corresponding information to a user is/are generated on an exceeding or a falling below of the range.

9. The method in accordance with claim 8, characterized in that an alarm is triggered and/or the output of corresponding information takes place as soon as the range for the sodium content or the range for the bicarbonate content is exceeded or fallen below depending on which exceeding or falling below takes place the sooner.

10. A preparation device for preparing a dialysis solution from at least two components, wherein the preparation device has a container having a bicarbonate component ("bicarbonate container") and a container having an acidic sodium component ("sodium container"); wherein the preparation device has a conductivity measurement cell for measuring the conductivity ($LF_{ist,Na}$) of a fluid after addition of the acidic sodium component to the fluid; a conductivity measurement cell for the measurement of the increase in conductivity ($\Delta LF_{ist,Bic}$) caused by addition of the bicarbonate component to the fluid; and a conductivity measurement cell for the measurement of the total conductivity ($LF_{ist,D}$) of the fluid containing the acidic sodium component and the bicarbonate component such that a dialysis solution is prepared; and wherein the preparation device is configured such that it checks whether the increase in conductivity ($\Delta LF_{ist,Bic}$) caused by the addition of the bicarbonate component is in an expected range of the increase in conductivity ($\Delta LF_{exp,Bic}$) and whether the measured total conductivity ($LF_{ist,D}$) is in an expected range of the total conductivity ($LF_{exp,D}$), with the named conductivity measurement cells being one and the same conductivity measurement cell, and the one and the same conductivity measurement cell being arranged downstream of the sodium container and downstream of the bicarbonate container.

11. The preparation device in accordance with claim 10, characterized in that the preparation device has an alarm unit and/or an output unit for outputting information to a user which is/are configured such that an alarm is triggered and/or information is output when the exceeding or falling below of the range is detected.

12. The preparation device in accordance with claim 10, characterized in that the preparation device has a main line into which a feed line in communication with the bicarbonate container opens and into which a further feed line in communication with the sodium container opens; and/or in that the main line is in communication with a container or with a source for water; and/or in that the conductivity measurement cell is arranged downstream of both openings of the feed lines.

13. The preparation device in accordance with claim 10, characterized in that the preparation device can be brought into fluid communication with a dialyzer of a dialysis machine so that the prepared dialysis solution flows through the dialysis side of the dialyzer; and in that the preparation device has a bypass line which leads around the dialyzer so that the prepared dialysis solution can be led around the dialyzer at times.

14. A dialysis machine having the preparation device in accordance with claim 10.

15. The preparation device of claim 12, wherein the source for water is RO water.

* * * * *